United States Patent [19]

Kuo et al.

[11] Patent Number: 5,349,099
[45] Date of Patent: Sep. 20, 1994

[54] PROCESS FOR PREPARING INTERMEDIATES FOR THE SYNTHESIS OF ANTIFUNGAL AGENTS

[75] Inventors: Shen-Chun Kuo, Union; Donald Hou, Verona; Zheng-Yun Zhan, Hillside, all of N.J.

[73] Assignee: Schering Corporation, Kenilworth, N.J.

[21] Appl. No.: 166,332

[22] Filed: Dec. 13, 1993

[51] Int. Cl.$^5$ .................. C07C 25/13; C07C 22/00
[52] U.S. Cl. ........................... 570/147; 570/142
[58] Field of Search .............. 570/142, 144, 147

[56] References Cited

U.S. PATENT DOCUMENTS

| 4,133,837 | 1/1979 | Markley | 570/142 |
| 4,935,564 | 6/1990 | Bunce et al. | 570/142 |
| 5,039,676 | 8/1991 | Saksena et al. | |

FOREIGN PATENT DOCUMENTS

| 332387 | 9/1989 | European Pat. Off. |
| WO89/04829 | 6/1989 | PCT Int'l Appl. |
| WO93/09114 | 5/1993 | PCT Int'l Appl. |

OTHER PUBLICATIONS

Konasu, et al. Tetrahedron Letters, vol. 32 (51) pp. 7545–7548 (1991).
Belsham, et al, *J. C. S. Perkin II*, pp. 119–125 (1974).

*Primary Examiner*—Johann Richter
*Assistant Examiner*—Kimberly J. Kestler
*Attorney, Agent, or Firm*—Paul A. Thompson

[57] ABSTRACT

Disclosed is a process for preparing allylic halides of the formula I

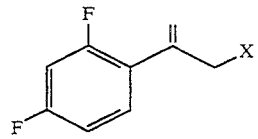

wherein X is Cl, Br or I, for use as intermediates in the synthesis of substituted tetrahydrofuran azole anti-fungal agents.

11 Claims, No Drawings

PROCESS FOR PREPARING INTERMEDIATES FOR THE SYNTHESIS OF ANTIFUNGAL AGENTS

BACKGROUND OF THE INVENTION

PCT International Publication No. WO 89/04829, U.S. Pat. No. 5,039,676, and PCT International Publication No. WO 93/09114 disclose substituted tetrahydrofuran azole compounds having utility as antifungal agents. A number of processes for the synthesis of these compounds are known. In addition, U.S. Ser. No. 08/055,268 describes a process for preparing chiral intermediates for use in the preparation of these antifungal agents. Dialkylmalonate derivatives of the formula IV

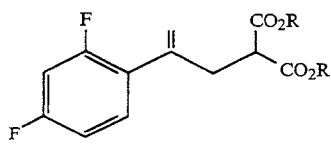

wherein R is $C_1$–$C_6$ alkyl, are important intermediates used in this process. An efficient synthesis of compounds of the formula IV is therefore a key factor in the synthesis of antifungal compounds via this process.

Preparation of compounds of the formula IV is most readily accomplished by the process described in U.S. Ser. No. 08/055,268. This process, as shown in Reaction 1, comprises reacting a dialkyl malonate anion, wherein $M^+$ is a suitable metal counterion and R is $C_1$–$C_6$ alkyl, with a compound of the formula V, wherein Z is a leaving group selected from Br, —$OSO_2CH_3$ or —$OSO_2C_6H_4CH_3$, to form a compound of formula IV. However, the prior art methods for preparing Reaction 1:

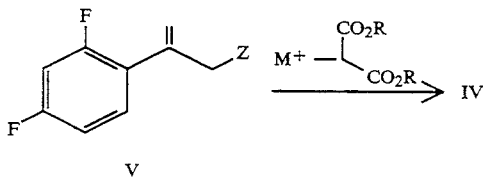

compounds of the formula V are typically low yielding, inefficient and not amenable to commercial scale synthesis. It is therefore desirable to develop a chemically efficient, high yield process for the synthesis of compounds of the formula V.

SUMMARY OF THE INVENTION

The present invention comprises a process for preparing allylic halide compounds of the formula I

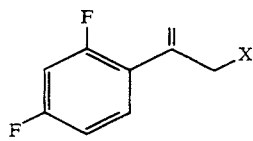

wherein X is Cl, Br or I, comprising dehydrating a tertiary alcohol of the formula II

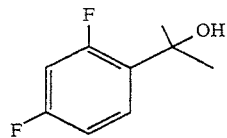

by heating in the presence of an acid to form an olefin of the formula III

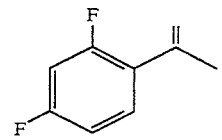

and treating the olefin III with a halogenating agent to form the allylic halide compound of formula I.

Preferred acids for dehydration of the tertiary alcohol include p-TsOH and $H_2SO_4$.

Preferably the olefin is treated with a halogenating agent selected from NCS or NBS. More preferably the halogenating agent is used in the presence of a catalyst to form a compound of the formula I wherein X is Br or Cl. Preferred catalysts include AIBN and organic peroxides, such as benzoyl peroxide.

In an alternative embodiment, the halogenating agent is selected from NCS, NBS or $I_2$, and is used in the presence of water to form a halohydrin of the formula VI

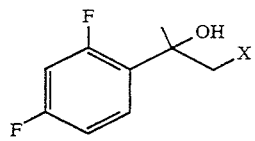

wherein X is Br, Cl or I, followed by dehydrating the halohydrin by heating in the presence of an acid to form a compound of the formula I wherein X is Br, Cl or I.

The present invention further comprises a process as described above wherein the tertiary alcohol of formula II is prepared by reacting 2',4'-difluoroacetophenone with an methylating agent. The methylating agent is an organometallic agent such as methyl grignard, e.g. $CH_3MgBr$, or methyllithium.

DETAILED DESCRIPTION

As used herein, the term
"halogenating agent" means a reagent capable of reacting with an allylic hydrocarbon moiety to form an allylic halide (e.g. bromide, chloride or iodide) or, in the presence of water, a halohydrin. Preferred halogenating agents include 1,3-dichloro-5,5-dimethylhydantoin, 1,3-dibromo-5,5-dimethylhydantoin, NCS, NBS and $I_2$;

"acid" means an organic or inorganic acid capable of catalyzing the dehydration of a tertiary alcohol to form an olefin, or a halohydrin to form an allylic halide, with preferred acids including p-TsOH and $H_2SO_4$;

"catalyst" means a substance capable of initiating reactions involving organic free radicals, such as AIBN and organic peroxides, e.g. benzoyl peroxide;

"Lewis acid" means a reagent capable of catalyzing a Friedel-Crafts reaction, such as AlCl₃, SnCl₄ or ZnCl₂;

"methylating agent" means an organometallic reagent capable of delivering a nucleophilic methyl group to the carbonyl carbon of a ketone to form a tertiary alcohol. Preferred methylating agents include methyl grignard and methyllithium.

The following solvents and reagents employed in the process of the present invention are identified by the abbreviations indicated: ethyl acetate (EtOAc); diethyl ether (Et₂O); ethanol (EtOH); tetrahydrofuran (THF); dimethylsulfoxide (DMSO); methanol (MeOH); N-chlorosuccinimide (NCS); N-bromosuccinimide (NBS); p-toluenesulfonic acid (p-TsOH); azobisisobutyronitrile (AIBN).

The present invention comprises a process as shown in Reaction Scheme A for preparing compounds of the formula I.

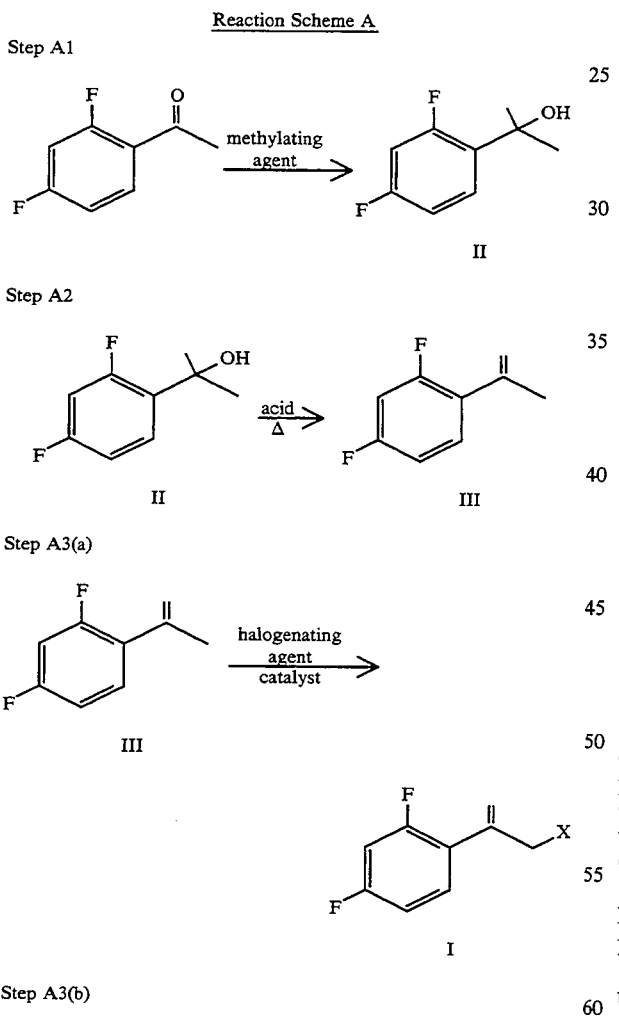

-continued
Reaction Scheme A

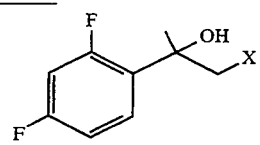

IV

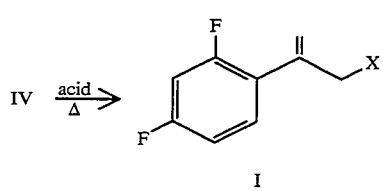

I

In Step A1, 2',4'-difluoroacetophenone is reacted with a methylating agent, preferably methyl grignard or methyllithium, in a suitable solvent, such as THF, CH₂Cl₂ or toluene, at 20° to −100° C., preferably at 0° to −80° C., to form a tertiary alcohol of the formula II.

Alternatively, the tertiary alcohol II is prepared by reacting p-difluorobenzene and acetone in a suitable solvent, such as CS₂ or CH₂Cl₂, in the presence of a suitable Lewis Acid, such as AlCl₃, SnCl₄ or ZnCl₂.

In yet another alternative, the tertiary alcohol II is prepared by treating 2,4-difluorobromobenzene with Mg in a suitable solvent, such as Et₂O, THF or toluene, to form the Grignard reagent and reacting the Grignard reagent with acetone to form the alcohol II.

In Step A2, the tertiary alcohol II is dehydrated by heating at 30° to 100° C., preferably at 50° to 90° C., in a suitable solvent, such as CH₂Cl₂ or toluene, in the presence of an acid, preferably pTsOH or H₂SO₄, to form the olefin III.

In Step A3(a), the olefin III is treated with a halogenating agent, such as NCS, 1,3-dichloro-5,5-dimethylhydantoin, NBS or 1,3-dibromo-5,5-dimethylhydantoin, in a suitable solvent, such as CCl₄, preferably in the presence of a catalyst, such as AIBN or an organic peroxide, such as benzoyl peroxide, at 50° to 150° C., preferably at 80° to 130° C., to form a compound of the formula I, wherein X is Cl or Br.

Alternatively, in Step A3(b), the olefin III is treated with a halogenating agent, such as NCS, NBS or I₂, in a suitable solvent, such as DMSO or CH₃CN, in the presence of water, at 0° to 120° C., preferably at 20° to 100° C., to form a halohydrin of the formula IV. The halohydrin is then dehydrated by heating at 30° to 100° C., preferably at 40° to 70° C., in a suitable solvent, such as CH₂Cl₂, in the presence of an acid, preferably p-TsOH, to form a compound of the formula I, wherein X is Br, Cl or I.

The starting compound 2',4'-difluoroacetophenone is known, and is commercially available or can be prepared by established methods.

The following preparations and examples are illustrative of the process of the present invention.

PREPARATION 1

Combine 8.11 g (52 mmol) of 2',4'-difluoroacetophenone and 45 mL of toluene and cool the mixture to −78° C. Slowly add 20 mL of a 3M solution of CH₃MgBr and stir the reaction mixture overnight. Quench the mixture with 50 mL of water and 20 mL of 1N HCl (aqueous), then extract with 50 mL of EtoAc. Concentrate the extract in vacuo to give 9.06 g of the tertiary alcohol product. ¹H NMR (CDCl₃): 7.60–7.54 (m, 1H); 6.89–6.78 (m, 2H); 2.10 (br s, 1H); 1.65 (s, 6H).

PREPARATION 2

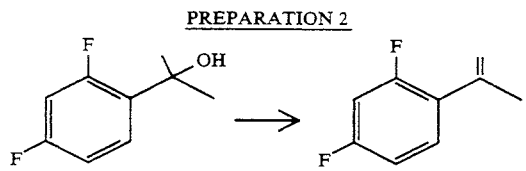

Combine 9.06 g of the product of Preparation 1 and 45 mL of toluene, add 0.65 g of H₂SO₄, and heat the mixture to 80°-−85° C. for 3 h. Quench the reaction mixture with 20 mL of 1N NaOH (aqueous) and extract with 50 mL of EtOAc. Concentrate the extract in vacuo to a residue. Distill the residue under vacuum to give 5.68 g of the olefin product. ¹H NMR (CDCl₃): 7.35–7.25 (m, 1H); 6.89–6.79 (m, 2H); 5.24 (d, 2H); 2.15 (s, 3H).

PREPARATION 3

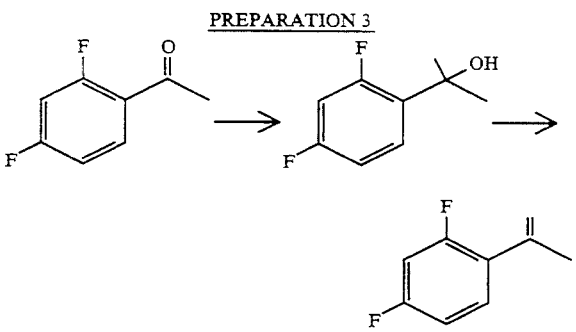

Slowly add a solution of 50 g of 2',4'-difluoroacetophenone in 100 mL of CH₂Cl₂ to a chilled (0° C.) mixture of 120 mL of 3M CH₃MgBr and 500 mL of CH₂Cl₂. Stir the resulting mixture at 0° C. for 30 min., then quench the reaction by slowly adding (dropwise) 50 mL of water. Stir the mixture for 20 min, then add 400 mL of 1N HCl (aqueous) and stir at room temperature for 30 min. Separate the organic and aqueous phases of the mixture and wash the organic layer with 300 mL of water, then with 300 mL of brine. Combine the aqueous solutions and extract with CH₂Cl₂ (2×150 mL). Combine the two organic extracts and wash with brine. Combine the extracts and the original organic solution, dry over MgSO₄, then filter and collect the filtrate.

Add 5 g of p-TsOH to the filtrate and distill the mixture (bath temperature at 70° C.) to remove 600 mL of CH₂Cl₂. Add 500 mL of CH₂Cl₂ and repeat the distillation. Repeat the addition distillation process with four more 500 mL portions of CH₂Cl₂, to give a final solution volume of @400 mL. Add 500 mL of saturated NaHCO₃ (aqueous) to the solution and stir for 2 h at room temperature. Separate the layers and concentrate the organic solution in vacuo (20 mm Hg) to a residue. Distill the residue at high vacuum (1.8 mm Hg) and collect the fraction boiling at 56°–58° C. to give 45 g of the olefin product.

PREPARATION 4

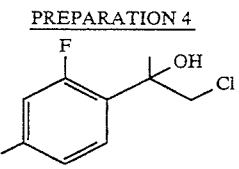

Combine 5 mL of a 3M solution of CH₃MgBr in Et₂O and 30 mL of CH₂Cl₂ and cool the mixture to 0° C. Add a solution of 3.0 g of α-chloro-2',4'-difluoroacetophenone in 10 mL of CH₂Cl₂ and stir at 0° C. for 10 min. Slowly add 1 mL of water, then 15 mL of 1N HCl (aqueous). Separate the layers and extract the aqueous layer with CH₂Cl₂ (2×10 mL). Combine the extracts and the original organic layer and wash with brine. Dry the solution over MgSO₄, then concentrate in vacuo to give 3.2 g of the chlorohydrin product. ¹H NMR (CDCl₃): 7.72–7.66 (m, 1H); 7.00–6.81 (m, 2H); 4.00 (d of d, 2H); 2.81 (br s, 1H); 1.69 (s, 3H).

EXAMPLE 1

Step A

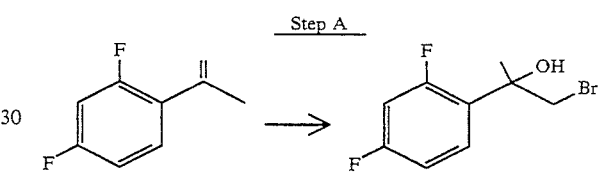

Combine 5.3 g of the olefin, 50 mL of DMSO and 1.5 mL of water. Carefully add 7.4 g of NBS in 5 portions and stir the resulting mixture at room temperature for 1 . Dilute the mixture with 200 mL of water, then extract with hexane (3×120 mL). Combine the extracts, wash the combined extracts with water, then with brine, and dry over MgSO₄. Concentrate in vacuo to give 8.3 g of the bromohydrin product. ¹H NMR (CDCl₃): 7.77–7.68 (m, 1H); 7.03–6.96 (m, 2H); 3.98 (d of d, 2H); 2.79 (br s, 1H); 1.78 (s, 3H).

The analogous chlorohydrin can be prepared via substantially the same procedure, by substituting NCS for NBS.

Step B

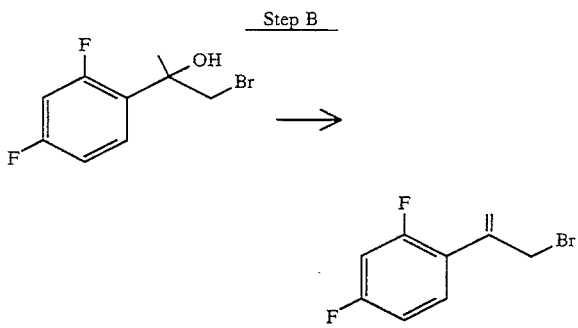

Combine 0.6 g of the bromohydrin product of Step A, 30 mg of p-TsOH and 30 mL of CH₂Cl₂. Distill the mixture (60° bath) to remove the bulk of the solvent, then add 30 mL of CH₂Cl₂ and distill again. Repeat the solvent addition/distillation process with 4 additional 30 mL aliquots of CH₂Cl₂, distilling to a residue. Dilute the residue with 30 mL of CH₂Cl₂, wash with saturated NaHCO₃ (aqueous), then with brine, and dry over MgSO₄. Concentrate in vacuo to a residue to give 0.56 g of the product. The product is a mixture of the desired allylic bromide (81.1%) and its vinyl bromide isomer, e.g. a compound of the formula

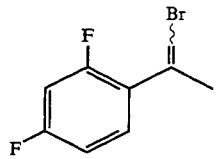

(18.9%) as determined by ¹H NMR integration. The allylic bromide product is characterized by ¹H NMR (CDCl₃): 7.46–7.30 (m, 2H); 6.97–6.84 (m, 1H); 5.51 (d, 1H); 4.47 (d, 1H); 4.39 (s, 2H).

Following substantially the same procedure, the iodohydrin product of Example 2 is converted to the allylic iodide of formula

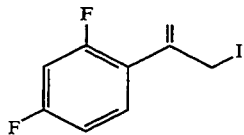

(96.4%), along with 3.6% of the isomeric vinyl iodide.

Similarly, using n-heptane as the solvent, the chlorohydrin product of Preparation 4 is converted to a 1:1 mixture of the allylic chloride and the isomeric vinyl chloride.

EXAMPLE 2

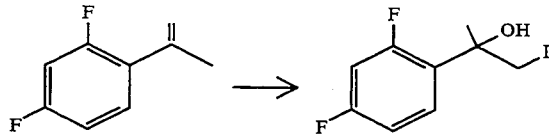

Combine 7.62 g of I₂, 3.51 g of KIO₃, 120 mL of water and 120 mL of CH₃CN, then add 1.5 mL of H₂SO₄, and a solution of 9.3 g of the olefin in 40 mL of 1:1 CH₃CN/water. Heat the resulting mixture to 100° C. for 30 min., then cool to room temperature. Dilute the mixture with water to a volume of 500 mL then treat the mixture with Na₂S₂O₃. Extract with EtOAc (3×150 mL), wash the combined extracts successively with Na₂S₂O₃ (aqueous), water, and brine. Dry the extracts over MgSO₄, and concentrate in vacuo to give 17.8 g of the iodohydrin product. ¹H NMR (CDCl₃): 7.64–7.56 (m, 1H); 6.93–6.77 (m, 2H); 3.80 (d of d, 2H); 2.47 (br s, 1H); 1.72 (s, 3H).

EXAMPLE 3

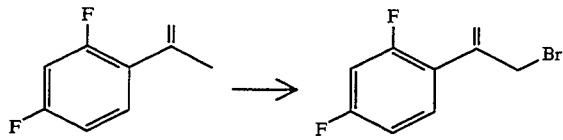

Combine 1.5 g of the olefin, 35 mL of CCl₄, 3.0 g of NBS and 0.07 g of benzoyl peroxide. Heat the mixture to 95°–100° C. for 3 days. Quench with 10 mL of 1N NaOH (aqueous) and 30 mL of water, then extract with CH₂Cl₂ (2×100 mL). Concentrate in vacuo to a residue. Chromatograph the residue (silica gel, 10% EtOAc/hexane) to give 1.37 g of the allylic bromide product.

EXAMPLE 4

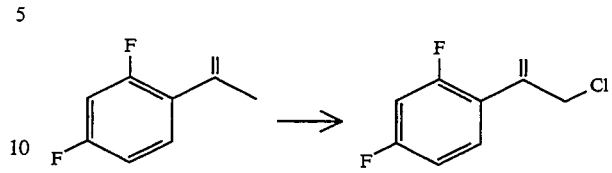

Combine 1.54 g of the olefin, 40 mL of chlorobenzene, 1.5 g of NCS and 50 mg of AIBN. Heat the mixture to 130° C. for 18 h. Cool the mixture to 0° C., filter to remove the solids and concentrate the filtrate in vacuo to give 1.86 g of the product. The product is an impure mixture comprising approximately 46% of the desired allylic chloride, and 31% of the vinyl chloride isomer.

EXAMPLE 5

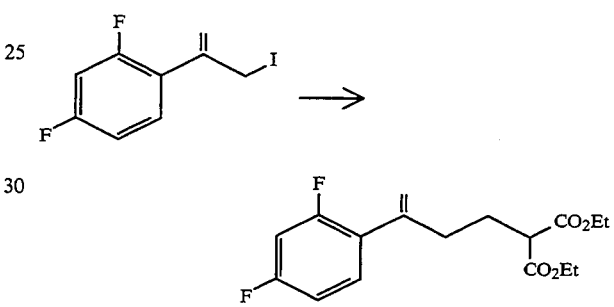

Combine 6.25 g of KOCH₃, 200 mL of EtOH and 13.6 mL of diethyl malonate and stir the mixture for 5 min. Add 40 mL of DMSO, stir for 10 min, then add a solution of 12.5 g of the allylic iodide of Example 2 in 40 mL of EtOH. Stir the mixture for 30 min, quench with 40 mL of water and 100 mL of 1N HCl (aqueous). Extract with n-heptane (3×250 mL), combine the extracts and wash the extracts with water, then with brine. Dry the extracts over MgSO₄, then concentrate in vacuo to give 13.3 g of the malonate product. ¹H NMR (CDCl₃): 7.30–7.19 (m, 1H); 6.89–6.78 (m, 2H); 5.25 (d, 2H); 4.17 (q, 4H); 3.41 (t, 1H); 3.08 (d, 2H); 1.12 (t, 6H).

We claim:

1. A process for preparing allylic halide compounds of the formula

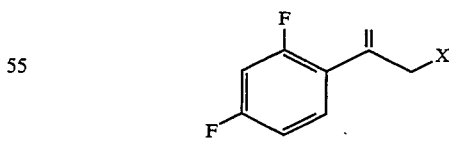

wherein X is Cl, Br or I, comprising dehydrating a tertiary alcohol of the formula

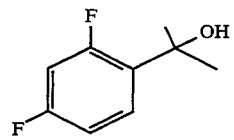

by heating in the presence of an acid to form an olefin of the formula

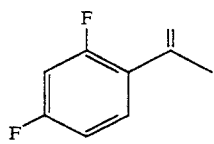

and treating the olefin with a halogenating agent to form the allylic halide.

2. The process of claim 1 wherein the acid for dehydration of the tertiary alcohol is p-toluenesulfonic acid or $H_2SO_4$.

3. The process of claim 2 wherein the halogenating agent is selected from N-chlorosuccinimide, 1,3-dichloro-5,5-dimethylhydantoin, N-bromosuccinimide or 1,3-dibromo-5,5-dimethylhydantoin.

4. The process of claim 3 wherein the halogenating agent is used in the presence of a catalyst.

5. The process of claim 4 wherein the catalyst is azobisisobutyronitrile or an organic peroxide.

6. The process of claim 5 wherein the organic peroxide is benzoyl peroxide.

7. The process of claim 2 wherein the halogenating agent is used in the presence of water, to form a halohydrin of the formula

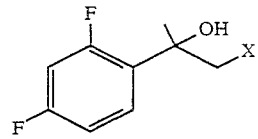

wherein X is Br, Cl or I, and the halohydrin is dehydrated by heating in the presence of an acid to form the allylic halide.

8. The process of claim 7 wherein the halogenating agent is selected from N-chlorosuccinimide, N-bromosuccinimide or $I_2$.

9. The process of claim 8 wherein the acid for dehydrating the halohydrin is p-toluenesulfonic acid.

10. The process of claim 1 wherein the tertiary alcohol is prepared by reacting 2',4'-difluoroacetophenone with a methylating agent.

11. The process of claim 10 wherein the methylating agent is $CH_3MgBr$, or methyllithium.

* * * * *